United States Patent [19]

Hennart et al.

[11] 4,249,029
[45] Feb. 3, 1981

[54] PROCESS FOR THE PREPARATION OF HIGHER ALKENES

[75] Inventors: Claude Hennart, Seraincourt; Georges Martin; Jean Favreau, both of Saint-Benoit, all of France

[73] Assignee: Airwick Industries, Inc., Carlstadt, N.J.

[21] Appl. No.: 61,347

[22] Filed: Jul. 27, 1979

[30] Foreign Application Priority Data

Aug. 8, 1978 [LU] Luxembourg .......................... 80093

[51] Int. Cl.$^3$ ................................................ C07C 1/00
[52] U.S. Cl. ...................................... 585/638; 585/469
[58] Field of Search ........................................... 385/638

[56] References Cited

U.S. PATENT DOCUMENTS

| 3,546,106 | 12/1970 | Blytas | 585/638 |
|---|---|---|---|
| 3,597,460 | 8/1971 | Thompson | 585/638 |
| 3,948,803 | 4/1976 | Carney | 585/638 |

OTHER PUBLICATIONS

Tetrahedron Letters, No. 42, pp. 3695–3698, 1977.

Primary Examiner—Curtis R. Davis
Attorney, Agent, or Firm—Harry Falber

[57] ABSTRACT

A process for the preparation of a straight-chain or branched alkene which has 20 to 24 carbon atoms and in which the ethylenic bond is located after a carbon atom numbered between 8 and 11, which process comprises reacting, in an anhydrous solvent, preferably in an oxahydrocarbon an organometallic copper compound with an alkyl or alkenylsulfonate.

8 Claims, No Drawings

PROCESS FOR THE PREPARATION OF HIGHER ALKENES

The present invention relates to a novel process for the preparation of higher alkenes.

Higher alkenes are understood as meaning alkenes, in the cis, trans or cis/trans configuration, which have between 20 and 24 carbon atoms and in which the double bond is located after a carbon atom numbered between 8 and 11.

Processes for the preparation of higher alkenes have already been described in U.S. Pat. No. 3,948,803. They comprise reacting, in a solvent which consists of tetrahydrofuran, an organo-magnesium compound consisting of an alkylmagnesium bromide with an alkenyl bromide in the presence of a catalyst which consists of a lithium chlorocyanocuprate or of a lithium dichlorocuprate.

The Applicant Company has found that, in place of the organo-magnesium compound, it is more advantageous directly to use an organometallic compound of copper or more particularly of copper/lithium.

The present invention thus relates to a process for the preparation of straight-chain or branched alkenes which have 20 to 24 carbon atoms and in which the ethylenic bond is located after a carbon atom numbered between 8 and 11, which process comprises reacting, in an anhydrous solvent, preferably in an oxahydrocarbon, an alkenyl(R)-copper or an alkenyl(R)-cuprolithium with an alkylsulfonate of the formula R'—O—SO$_2$—R'', or reacting an alkyl(R')-copper or an alkyl(R')-cuprolithium with an alkenylsulfonate R—O—SO$_2$—R'', R being an alkenyl radical which has 9 to 22 carbon atoms and in which the ethylenic bond is located after a carbon atom numbered between 8 and 11, counting from the opposite end of the chain to that carrying the copper, and R' being an alkyl radical having 1 to 15 carbon atoms, R and R' together having 20 to 24 carbon atoms, and R'' being a lower alkyl radical having 1 to 5 carbon atoms or a phenyl or tolyl radical.

Suitable oxahydrocarbons are all those known to be suitable for organometallic reactions, for example ethyl ether, propyl ether, butyl ether, tetrahydrofuran, tetrahydropyran and dioxan. They must be used in the anhydrous form. They can be used in the pure form or as a mixture with an anhydrous aromatic hydrocarbon.

The reaction temperature is below +20° C. Preferably, it is between −60° and 0° C., but it can also be below −60° C.

In general, the organometallic compound is first prepared in solution and the sulphonate is reacted with it by introducing the sulphonate into the reaction medium.

The organometallic compounds are prepared by known techniques. Preferred organometallic compounds are the cuprolithium compounds which are easily obtained by the reaction, in an anhydrous solvent, of cuprous iodide with an organo-lithium compound of the formula R—Li or R'—Li, the latter compound being prepared by the reaction of metallic lithium with an alkyl(R') halide or alkenyl(R) halide.

The sulfonate is added either all at once or in small portions, but always taking care to maintain the low temperature of the reaction mixture.

A stoichiometric amount of the organometallic compound can be used, or the compound can be used in excess, which can be up to 100%.

The mixture is kept at a low temperature for several hours and is then allowed to warm up to ambient temperature and is left at this temperature for several hours, overnight for example, and is then treated in the conventional manner in order to extract the alkene formed. The reaction mixture is poured into water, to which a salt, such as sodium chloride, ammonium chloride or sodium sulfate has advantageously been added in order to facilitate separation of the product formed. The resulting mixture can be extracted with a solvent, for example pentane or petroleum ether, but this extraction is usually unnecessary, the solvent in the reaction mixture being sufficient to achieve good separation. The organic layer is washed with water and the solvent is then removed by distillation. The residue comprises the desired alkene and by-products.

The alkene can be separated off by known means, such as by vacuum distillation, but it is generally not necessary to isolate the alkene if it is to be used as a lure. An additional advantage of this invention is, in fact, that crude products are obtained in which the impurities are in no way troublesome when the product is used.

These impurities in no way change the luring power of the present alkene for the insects; they merely play a passive role as a simple diluent, without any repellent effect. This is particularly important inasmuch as it enables lures to be prepared as the crude reaction products without necessitating any isolation or any long, delicate and costly purification.

A further advantage of the process according to the invention is that it, like the initial invention, makes it possible, using simple and inexpensive starting materials, to obtain products in which the steric configuration of these starting materials is maintained. The ethylenic starting materials are obtained from known oleyl or erucyl alcohols or from alcohols which can be prepared from dihydropyran and an alkylmagnesium halide according to known processes (C.R. Acad. Sci., 1934, 198, 1246; Bul. Soc. Chim., 1935, 2, 311; J. Am. Chem. Soc., 1950, 72, 1490 and 2120; J. Chem. Soc., 1950, 1712; and J. Am. Chem. Soc., 1954, 76, 4538).

The process according to the invention is illustrated by the following examples.

EXAMPLE 1

Cis-tricos-9-ene 38 grams (0.2 mol) of cuprous iodide dispersed in 150 ml of anhydrous benzene are introduced into a one liter three-necked flask. The dispersion is cooled to about −30° C. and a solution, in 60 ml of ethyl ether, of pentyl-lithium obtained from 6 grams (0.86 mol) of lithium and 61 grams (0.4 mol) of pentyl bromide is added, with stirring and without allowing the temperature to rise.

The temperature is lowered to about −70°/−80° C. and 42.2 grams (0.1 mol) of oleyl tosylate dissolved in 50 ml of ethyl ether are added, with stirring. The rate of introduction is regulated so that the temperature does not rise above −70° C. The reaction mixture is stirred at −70°/−80° C. for two hours and is then allowed to warm up again to ambient temperature, with continued stirring.

The mixture is poured into 300 ml of water saturated with ammonium chloride and the resulting mixture is stirred for a few minutes. The organic phase is separated off and is washed with water and dried over anhydrous magnesium sulfate. The solvents are removed in vacuo in a rotary evaporator.

This yields 31 grams of a clear oily product containing 94% of cis-tricos-9-ene.

EXAMPLE 2

Cis-tricos-9-ene

Example 1 was repeated, using five times the quantities of the reactants.

This yielded 162 grams of the same product as in Example 1, containing 93% of cis-tricos-9-ene.

EXAMPLE 3

Cis-heneicos-9-ene

Example 1 is repeated, using propyl-lithium prepared from 50 grams of propyl bromide.

This yields 38 grams of a clear oily product containing 73% of cis-heneicos-9-ene.

EXAMPLE 4

Cis-docos-9-ene

Example 1 is repeated, using butyl-lithium prepared from 55 grams of butyl bromide.

This yields 36 grams of an amber-coloured oily product containing 82% of cis-docos-9-ene. By rectification in vacuo, 26.8 grams of cis-docos-9-ene with a purity of almost 100% are isolated.

EXAMPLE 5

Cis-21-methyl-docos-9-ene

Example 1 is repeated, using 3-methyl-butyl-lithium prepared from 61 grams of 3-methyl-butyl bromide.

This yields 52 grams of a clear oily product containing 56% of cis-21-methyl-docos-9-ene.

EXAMPLE 6

Cis-tetracos-9-ene

Example 1 is repeated, using hexyl-lithium prepared from 67 grams of hexyl bromide.

This yields 56 grams of a clear oily product containing 59% of cis-tetracos-9-ene.

EXAMPLE 7

Cis-eicos-9-ene

Example 1 is repeated, using ethyl-lithium prepared from 63 grams of ethyl iodide.

This yields 31 grams of a clear oily product containing 86% of cis-eicos-9-ene.

EXAMPLE 8

Cis-tricos-9-ene 95 grams (0.5 mol) of cuprous iodide dispersed in 500 ml of anhydrous tetrahydrofuran are introduced into a three liter, three-necked flask.

The dispersion is cooled to about −30° C. and a solution, in 150 ml of tetrahydrofuran, of methyl-lithium obtained from 14 grams (2 mols) of lithium and 142 grams (1 mol) of methyl iodide is added, with stirring and without allowing the temperature to rise. The temperature is lowered to between −70° and −80° C. and 100 grams (0.25 mol) of erucyl mesylate (i.e. cis-docos-9-enyl methane-sulfonate) dissolved in 150 ml of tetrahydrofuran are added, with stirring and without the temperature rising above −70° C. The reaction mixture is stirred at this temperature for three hours and is then allowed to warm up again to ambient temperature, with continued stirring.

The mixture is poured into one liter of water saturated with sodium sulfate and the resulting mixture is then stirred for several minutes. The organic phase is separated off and is washed with cold water and dried over dry calcium sulfate.

The solvent is removed in vacuo in a rotary evaporator.

This yields 88 grams of an amber-coloured oily product containing 73% of cis-tricos-9-ene.

EXAMPLE 9

Cis-tetracos-9-ene

Example 8 is repeated, using ethyl-lithium prepared from 156 grams of ethyl iodide.

EXAMPLE 10

Cis-tricos-9-ene 95 grams (0.5 mol) of cuprous iodide dispersed in 600 ml of anhydrous dioxan are introduced into a five liter three-necked flask.

The dispersion is cooled to about −30° C. and a solution, in 300 ml of ethyl ether, of oleyl-lithium obtained from 14 grams (2 mols) of lithium and 332 grams (1 mol) of oleyl bromide is added, with stirring and whilst maintaining the same temperature.

The temperature is lowered to between −70° and −80° C. and 57 grams (0.25 mol) of pentyl benzene-sulfonate dissolved in 100 ml of ethyl ether are added, with stirring and without the temperature rising above −70° C.

The reaction mixture is kept at this temperature for four hours, with constant stirring, and is then allowed to warm up to ambient temperature, with continued stirring. The mixture is then poured into 1.5 liters of water saturated with sodium chloride and the resulting mixture is stirred for several minutes. The organic phase is separated off and is washed and dried over anhydrous magnesium sulfate. The solvents are removed in vacuo in a rotary evaporator.

This yields 82 grams of a virtually colourless, oily product containing 91% of cis-tricos-9-ene.

EXAMPLE 11

Cis-docos-9-ene

Example 10 is repeated, using 53.5 grams of butyl benzene-sulfonate.

This yields 86 grams of a yellowish oily product containing 81% of cis-docos-9-ene.

EXAMPLE 12

Cis-docos-8-ene

Example 10 is repeated, using 81.5 grams of cis-dodec-4-enyl benzene-sulfonate and decyl-lithium prepared from 268 grams (1 mol) of decyl iodide.

This yields 78 grams of a pale yellow oily product containing 84% of cis-docos-8-ene.

EXAMPLE 13

Cis-tetracos-10-ene

Example 10 is repeated, using 59 grams of decyl mesylate and cis-tetradec-4-enyl-lithium prepared from 275 grams of cis-tetradec-4-enyl bromide.

This yields 92 grams of a clear oily product containing 89% of cis-tetracos-10-ene.

EXAMPLE 14

Cis-2-methyl-docos-8-ene

Example 10 is repeated, using 59 grams of decyl mesylate and cis-10-methyl-dodec-4-enyl-lithium prepared from 261 grams of cis-10-methyl-dodec-4-enyl bromide.

This yields 92 grams of a yellowish oily product containing 81% of cis-2-methyl-docos-8-ene.

EXAMPLE 15

Cis-tricos-11-ene

Example 10 is repeated, using 92 grams of cis-pentadec-4-enyl benzene-sulfonate and octyl-lithium prepared from 240 grams of octyl iodide.

This yields 86 grams of a pale yellow oily product containing 87% of cis-tricos-11-ene.

EXAMPLE 16

Trans-22-methyl-tricos-9-ene

Example 10 is repeated, using 62.5 grams of isoundecyl mesylate and trans-tridec-4-enyl-lithium prepared from 261 grams of trans-tridec-4-enyl bromide.

This yields 90 grams of an amber-coloured oily product containing 82% of trans-22-methyl-tricos-9-ene.

EXAMPLE 17

Cis/trans-tricos-9-ene

Example 10 is repeated, using 59 grams of decyl mesylate and cis/trans-tridec-4-enyl-lithium prepared from 261 grams of cis/trans-tridec-4-enyl bromide.

This yields 92 grams of an amber-coloured oily product containing 71% of cis/trans-tricos-9-ene.

EXAMPLE 18

Cis/trans-docos-9-ene

Example 10 is repeated, using 55.5 grams of nonyl mesylate and cis/trans-tridec-4-enyl-lithium prepared from 261 grams of cis/trans-tridec-4-enyl bromide.

This yields 88 grams of a clear yellow oily product containing 74% of cis/trans-docos-9-ene.

The process according to the invention is particularly advantageous since it avoids the use of a catalyst and nevertheless makes it possible to obtain, in excellent yields, crude products which have a very high concentration of active alkene compound and can be directly used as lures for anthropophilic flies in bait compositions.

What is claimed is:

1. A process for the preparation of a straight-chain or branched alkene which has 20 to 24 carbon atoms and in which the ethylenic bond is located after a carbon atom numbered between 8 and 11, which process comprises reacting, in an anhydrous solvent, an organometallic copper compound consisting of alkenyl(R)-copper or alkenyl(R)-cuprolithium with an alkylsulfonate of the formula $R'$—O—$SO_2$—$R''$, R being an alkenyl radical which has 9 to 22 carbon atoms and in which the ethylenic bond is located after a carbon atom numbered between 8 and 11, counting from the opposite end of the chain to that carrying the copper, and $R'$ being an alkyl radical having 1 to 15 carbon atoms, R and $R'$ together containing 20 to 24 carbon atoms, and $R''$ being a lower alkyl radical having 1 to 5 carbon atoms or a phenyl or tolyl radical.

2. A process for the preparation of a straight-chain or branched alkene which has 20 to 24 carbon atoms and in which the ethylenic bond is located after a carbon atom numbered between 8 and 11, which process comprises reacting, in an anhydrous solvent, an organometallic compound consisting of alkyl($R'$)-copper or alkyl($R'$)-cuprolithium with an alkenylsulfonate R—O—$SO_2$—$R''$, R being an alkenyl radical which has 9 to 22 carbon atoms and in which the ethylenic bond is located after a carbon atom numbered between 8 and 11, counting from the opposite end of the chain to that carrying the copper, and $R'$ being an alkyl radical having 1 to 15 carbon atoms, R and $R'$ together containing 20 to 24 carbon atoms, and $R''$ being a lower alkyl radical having 1 to 5 carbon atoms or a phenyl or tolyl radical.

3. A process according to claim 1 or claim 2, wherein the anhydrous solvent is an oxahydrocarbon.

4. Process according to claim 2, wherein the anhydrous solvent is selected from ethyl ether, propyl ether, butyl ether, tetrahydrofuran, tetrahydropyran, dioxan, mixtures of these solvents with one another and mixtures of one or more of these solvents with one or more anhydrous hydrocarbons.

5. A process according to claims 1 or 2, wherein the reaction is carried out at a temperature below +20° C.

6. A process according to claims 1 or 2, wherein the reaction is carried out at a temperature of between −60° C. and 0° C.

7. A process according to claims 1 or 2, wherein the reaction is carried out at a temperature below −60° C.

8. A process according to claims 1 or 2, wherein the organometallic compound is used in an amount which is between the stoichiometric amount and twice the stoichiometric amount.

* * * * *